United States Patent [19]
Johansson et al.

[11] Patent Number: 6,147,750
[45] Date of Patent: Nov. 14, 2000

[54] DETERMINATION OF GLOSS QUALITY

[75] Inventors: Per-Åke Johansson, Stockholm; Mikael Lindstrand, Solna, both of Sweden

[73] Assignee: STFI, Stockholm, Sweden

[21] Appl. No.: 09/125,839
[22] PCT Filed: Jan. 29, 1997
[86] PCT No.: PCT/SE97/00135
§ 371 Date: Oct. 26, 1998
§ 102(e) Date: Oct. 26, 1998
[87] PCT Pub. No.: WO97/32196
PCT Pub. Date: Sep. 4, 1997

[30] Foreign Application Priority Data

Feb. 29, 1996 [SE] Sweden ................................. 9600816

[51] Int. Cl.[7] ............................................. G06K 9/74
[52] U.S. Cl. .................................. 356/71; 356/445
[58] Field of Search ........................ 356/71, 445, 448

Primary Examiner—Robert H. Kim
Assistant Examiner—Amanda Merlino
Attorney, Agent, or Firm—John Lezdey

[57] ABSTRACT

A method and apparatus for obtaining a basis on which the gloss quality of a sample surface of a sample, such as a paper sheet, can be determined by illuminating the sample surface and registering the intensity of the reflected light. With the intention of enabling several different types of gloss variation investigations to be made on a sample surface essentially in accordance with known principles of gloss facet approximation, it is proposed, among other things, that the sample surface is exposed in an image registering area by controlled rotary movement of the sample surface through the image registering area or by controlled rotary movement of the image registering area over the sample surface, wherein the intensity of the light reflected from a plurality of spatially well defined part-surfaces of the sample surface is registered several time during this rotary movement while, at the same time, determining the positions of the part-surfaces in the image registering area, and in turn the viewing angle, so as to establish what we here define as an image volume which is representative of the registered light intensity as a function of the position of the part-surfaces within the sample surface and of the respective viewing angle.

15 Claims, 5 Drawing Sheets

DETERMINATION OF GLOSS QUALITY

FIELD OF THE INVENTION

The present invention relates to a method and to apparatus which will provide a basis on which the gloss quality of a sample surface on a sample, such as a paper sheet, can be determined by illuminating the sample surface and registering the intensity of the light reflected therefrom.

BACKGROUND OF THE INVENTION

The gloss of, e.g., paper products such as LWC-paper has been measured with a large number of different methods over a long period of time. The majority of these methods, and primarily the normative methods, are concentrated on mean gloss levels over a large surface area. Since the mean gloss level is not the only parameter contributing to the subjective impression of gloss quality, there is a need of an evaluation method that conforms better to the human evaluation of gloss quality, which includes the perception of gloss variation.

When studying the phenomena of gloss, particularly of printed paper, it has been found that the main caracteristics of the gloss variation can be described if the surface of the paper is approximated by a model surface comprising small flat surface elements, gloss facets, wherein gloss variation is determined on the basis of the orientation of the individual facets with respect to the plane of the paper and the reflected intensity of the individual facets. However, no method and apparatus that can be used in practice have been proposed for determining gloss variations based on this gloss facet approximation.

One object of the present invention is to provide a method and apparatus of the aforesaid kind which can be used effectively to carry out a multiple of different types of gloss variation evaluations on a sample surface in accordance with the principles of the aforesaid gloss facet approximation.

The object is achieved with the features set forth in the following claims.

SUMMARY OF THE INVENTION

According to one aspect of the invention, the sample surface is exposed in an image registering area by controlled rotary movement of the sample surface through the image registering area, or by controlled rotary movement of this image registering area over the sample surface, wherein the intensity of light reflected from a plurality of spatially well defined part-surfaces of the sample surface is registered several times during such rotary movement while, at the same time, determining the position, and in turn the viewing angle of respective part-surfaces in the image registering area so as to establish, what we here define as an image volume representative of registered light intensity as a function of the position of said part-surfaces within the sample surface and of the viewing angle.

Because registration is effected during said rotary movement, e.g. rotary movement of the sample surface through the image registering area, it is possible to obtain a well adapted variation of the viewing angle; in other words light reflected from the sample surface can be registered from a sufficiently large variation of angles of incidents. Compilation of an image volume of the registered light intensities enables different types of gloss quality evaluations of the sample surface to be carried out effectively during the registration process, or separately on the basis of the stored image volume.

When the sample surface is brought to a specific convex-curve shape prior to exposure in the image registering area, there is obtained an appropriately large spread of the viewing angle in conjunction with said rotary movement, as compared with a flat sample surface.

When the sample surface is given a circular-cylindrical shape and exposed in the registering area by rotating the cylinder about its centre axis, the sample can be mounted on the end of a simple mechanically rotatable shaft, drum or the like, so that each part-surface can be moved through the image registering area in a readily controlled manner.

Other features of the invention and advantages afforded thereby will be evident from the following claims and also from the following description.

The invention will now be described in more detail with reference to exemplifying embodiments thereof and also with reference to the accompanying diagrammatic drawings, in which

BRIEF DESCRIPTION OF THE DRAWINGS

Figure 1:
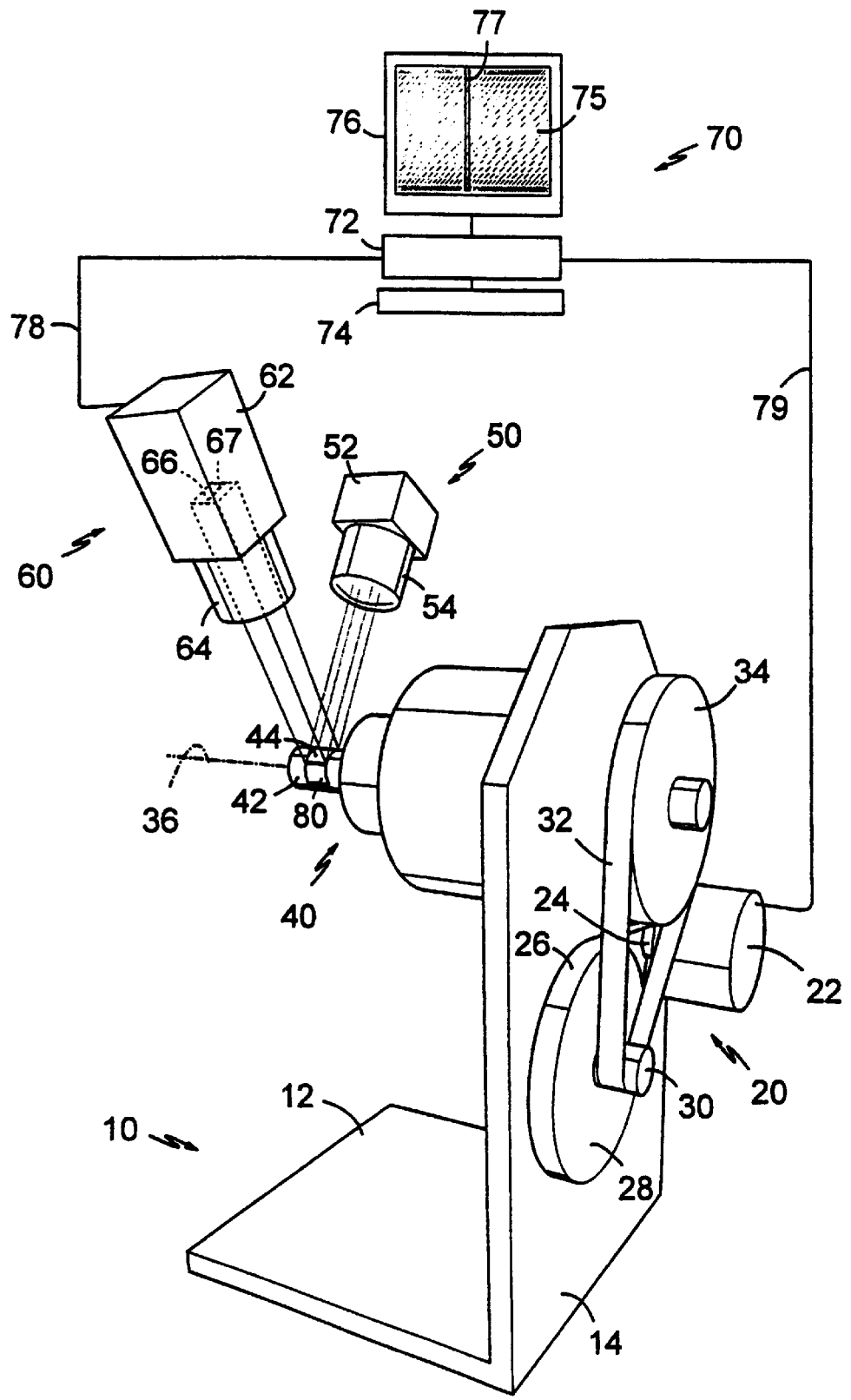
FIG. 1 is a perspective view of one possible apparatus according to the invention.

The apparatus illustrated in FIG. 1 for obtaining a basis on which gloss quality can be determined in accordance with the invention includes generally an L-shaped angled stand 10 having a drive unit 20 for a sample holder 40 which exposes a sample 80 in an image registering area of a camera 60, said sample being illuminated by a light source 50. The images registered in the camera are processed in an image processing unit 70, such as a personal computer, which is also adapted to control the drive unit of the sample holder 40.

Although not shown in detail, the drive unit 20 includes a stepping motor 22 that is firmly mounted on a vertical wall 14 of the stand 10 and which drives the sample holder 40 through the medium of a reduction gear mechanism journalled on the vertical wall 14 in accordance with the following: A first smaller toothed wheel 24 on the output shaft of the stepping motor 22 drives a first larger toothed wheel 28 through the medium of a first endless toothed belt 26. Fixedly mounted on the shaft of the toothed wheel 28 is a second smaller toothed wheel 30 which drives a second larger toothed wheel 34 through the medium of a second endless toothed belt 32.

In the illustrated embodiment there is used a stepping motor that has a resolution of 6000 steps/rev, wherein the reduction gear mechanism provides a reduction of about 1:46, so that the sample holder 40 connected directly to the shaft 36 of the toothed wheel 34 obtains a total resolution of about 280,000 steps/rev. This arrangement of toothed wheels and toothed belts enables the angle play of the sample holder 40 to be maintained at a level which is negligible in the present context, despite the high reduction. The sample holder 40 can thus be rotated in small angular steps around the shaft 36. The free end of the shaft 36 carries a stub shaft on whose cylindrical surface 42 the sample having a sample surface 80 whose gloss variation is to be evaluated is mounted in uniform abutment therewith. The radius of the cylindrical surface 42 may typically be about 8 mm, although other radii may be used as evident from the shouldered sample holder 40 shown in FIG. 1. A printed piece of rectangular LWC-paper is one example of a typical sample in this regard.

The light source 50 and the camera 60 are fixedly mounted with their respective optical axes located in a vertical plane that extends through the image registering area 44 defined on the cylinder surface 42. The angle between the optical axes approximately coincident on the image registering area shall be such as to enable the whole of the curved image registering area to be projected in the schematically indicated image plane 66 of the camera 60.

The light source 50 includes a lamp housing 50 and a lens system 54, and may consist of conventional microscope lighting.

The camera 60 used in the illustrated embodiment includes a camera housing 62 having a CCD-type image detector (CCD Charge Coupled Device) and a 60 mm camera objective 64.

The arrangement is furthermore such that the image of the image registering area 44 recorded by the camera in an image plane 66 is transferred through cable 78 to a computer 72 in the image process unit 70 for storage and further processing of information. The image being processed can be shown on a monitor 76 and image processing can be controlled externally by an input unit 74, such as a keyboard which is also able to control the stepping motor 22 via the computer 72 and a cable 79. In a stationary mode in which the camera 60 registers a curved object with relatively high surface fineness, such as the metal surface of the stub axle 42 in the image registering area 44, there is thus presented on the monitor 76 a digitalized image of the curved metal surface. The image may have a spatial resolution of 512×512 picture elements (pixels). Although not necessary, the number of steps or increments through which the stepping motor needs to rotate in order to advance the sample surface into and out of the image registering area 44 may have a corresponding value, wherein the later described image volume may then have a resolution of 512×512×512 image volume elements (voxels). The gloss of the surface resulting from the reflected light appears on the image as a horizontal light band 75. A simple measure of the gloss quality of the surface is therewith the width of the band 75, i.e. a surface of high surface fineness produces a narrower band 75 than a surface of poorer surface fineness.

Figure 2:
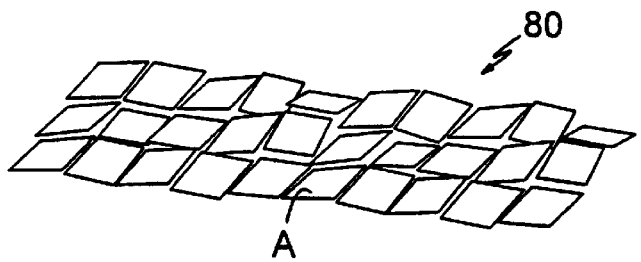
FIG. 2 illustrates a facet model of a sample surface.

In evaluating the gloss quality of paper, particularly of printed paper, it is often of interest to ascertain as well the intensity as the angular spread of the reflected light, which may, for instance, be a measurement of the extent to which a viewer of a page in a magazine needs to tilt this page of the magazine away from an angle of maximum light reflection intensity in order to satisfactorily discern the information printed on said page. The angular spread of the reflected intensive light, troublesome to the viewer, has been found to be mainly due to light scattering that can be explained with a model such as that illustrated schematically in FIG. 2, in which the paper surface 80 is seen as being comprised of discrete gloss facets A, i.e. small planar surface regions which, with regard to their ability to reflect light, can be considered to have a specific or most representative angle of inclination relative to the anticipated or ideal normal plane of the paper.

Figure 3:
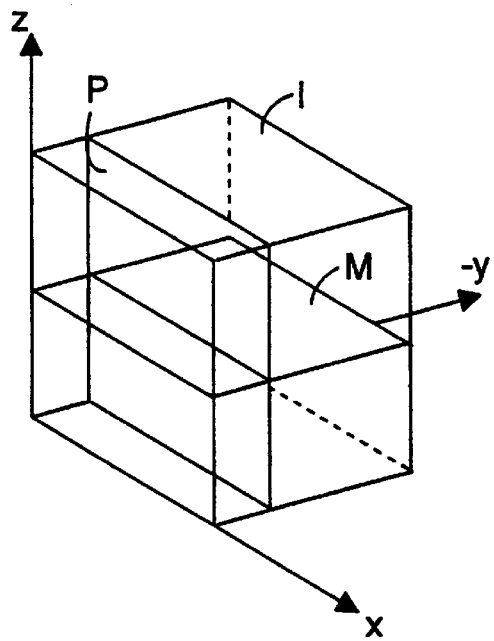
FIG. 3 is a simplified graphic presentation of an image volume.

In the following description, data is stored in the form of an image volume intended for use as a representation of the light reflection properties of a sample surface, more specifically a function I f(x,y,z), of FIG. 3, where the I-value is the intensity of registered light in the coordinate (x, y, z), wherein the x-y-values represent the position within the sample surface and the z-values represent the viewing angle.

Figure 4:
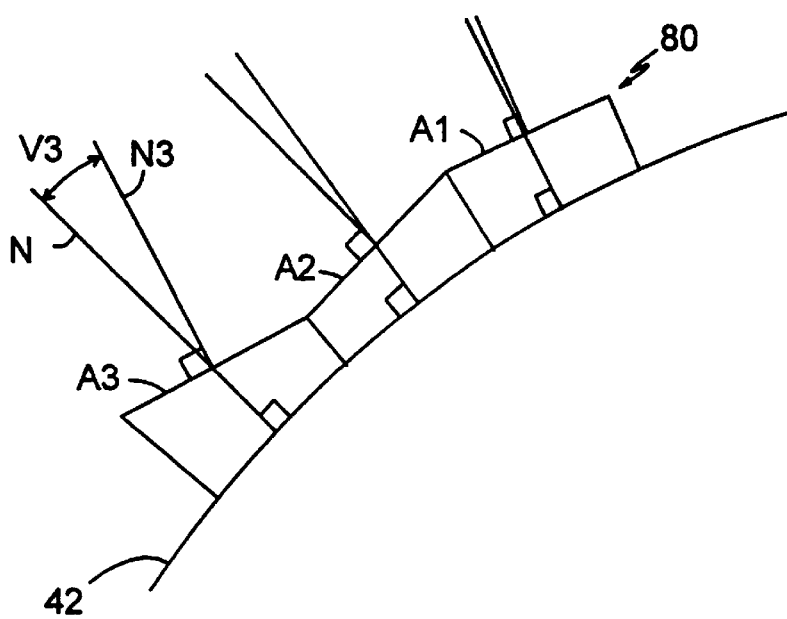
FIG. 4 is a side view of a part-area of a sample surface, exhibiting three facets.
Figure 5:
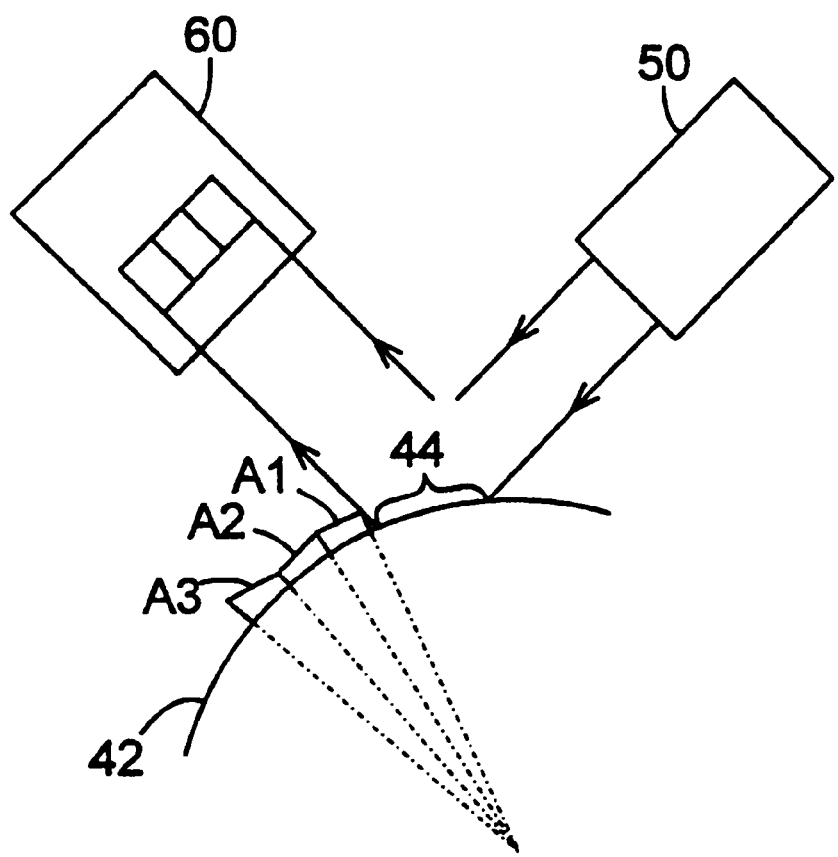
FIG. 5 is a side view corresponding to FIG. 4 prior to a simplified registering sequence in accordance with the invention.

Such an image volume can be compiled with the inventive apparatus and inventive method in the following manner:

FIGS. 4 and 5 illustrate schematically and inside view a sample 80 which, with the intention of facilitating the description and an understanding thereof, can be considered simply to comprise solely three part-surfaces A1, A2 and A3, which are also considered in one dimension, so as to compile an x-z-plane P (FIG. 3) in the image volume. Thus, solely "bands" 67 and 77 (FIG. 1) are registered in the image plane 66 of the camera 60 and in the image or picture displayed on the monitor 76.

Figure 6:
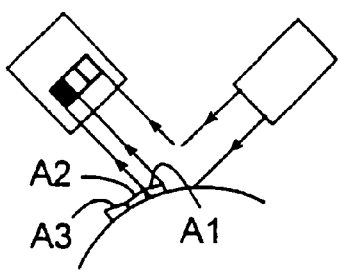
FIG. 6A–E illustrate the various steps during the simplified registering sequence.
Figure 6:
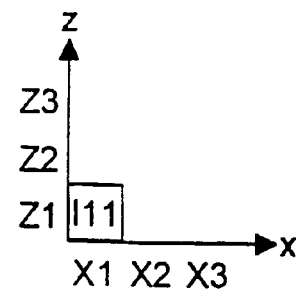
Figure 6:
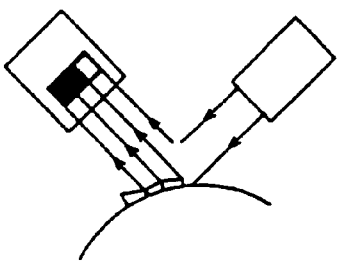
Figure 6:
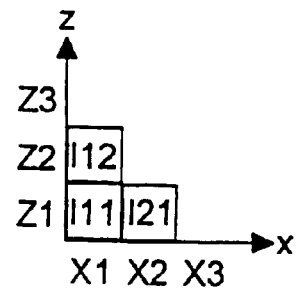
Figure 6:
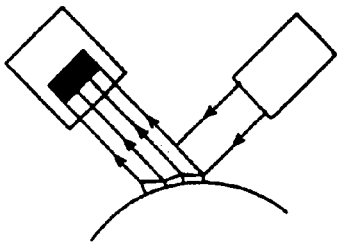
Figure 6:
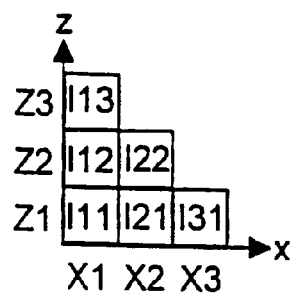
Figure 6:
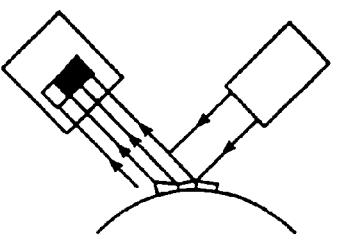
Figure 6:
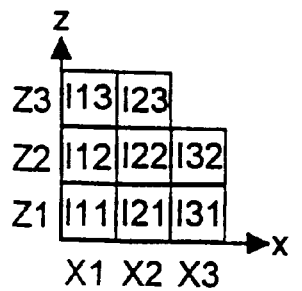
Figure 6:
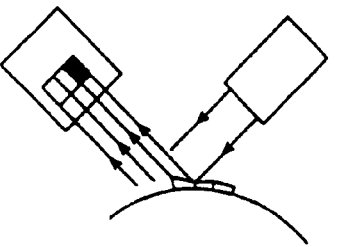
Figure 6:
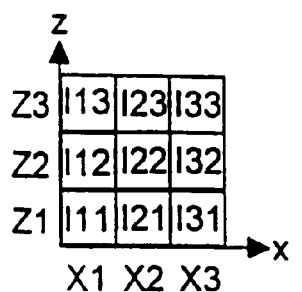

Beginning from the position shown in FIG. 5, the sample surface 80 in uniform abutment with the cylinder surface 42, e.g. firmly fixed by adhesive tape thereon, is advanced through the image registering area 44 in five steps to the positions A, B, C, D, E according to FIG. 6, wherein there is registered in each position the intensity of the light reflected from the part-surfaces A1, A2, A3 that are situated simultaneously in said image registering area 44 on the one hand, and the respective x- and z-coordinates of the part-surfaces on the other hand.

Thus, in position A the image volume obtains its first element I11 representing the light intensity at the position X1 and the viewing angle Z1 with respect to the part-surface A1 within the sample surface 80.

In position B the sample surface 80 has been advanced one further step, so that the part-surface A2 is in the place that was previously occupied by the part-surface A1, which has now been moved to a new position. Consequently, two further elements I12 and I21 have been added to the image volume, these elements representing the intensities of the part-surfaces A1 and A2 respectively, and the respective coordinates (X1, Z2) and (X2, Z1) (position, viewing angle).

In position C the sample surface has been advanced yet another step in a corresponding manner, so that the image volume now obtains an element from the newly advanced part-surface A3, in addition to the contributions from the earlier advanced part-surfaces A1 and A2, wherein all three sample surfaces are situated within the image registering area. The image volume has thus obtained the diagonal elements I13, I22 and I31 in this position.

In the terminating steps D and E, the elements I23, I32 and I33 are completed analogously with the view x-z-plane of the preceding image volume.

The complete image volume is compiled by registering all "bands" 67 (FIG. 1) over the full width of the image plane 66 analogously with what has been described above. This is preferably carried out so that the intensity of all y-coordinates will be registered for each pair of said z-x-coordinates in each position A–E.

In this regard it can be mentioned that although in the earlier description the part-surfaces have been described as being advanced in steps, the stepping motor 22 can be replaced by a continuously driven motor and the image registering area can be registered or scanned instantaneously by short camera exposures or stroboscopically at appropriately selected time intervals.

Depending on requirements, the image volume can either be analyzed in real time during its compilation, by saving only those image volume elements that fulfil a given search criterion with regard to gloss variation, or can in complete be stored in the computer 72 of the image processing unit for separate analysis. In the former case, the often large number of elements that do not fulfil the search criterion are rejected, so as to enable memory capacity and possibly processor capacity to be released, e.g., for video processing and presentation of search hits in an appropriate manner. In the latter case, the complete image volume is available for each desired type of gloss quality determination based on created criteria for evaluation.

Extracting the z-values of those volume elements that present maximum registered light intensity for each part-surface, i.e. for each pair of the x-y-value, is one example of a type of gloss quality determination that can be carried out directly during compilation of the image volume. In the case of an ideal smooth mirror-like sample surface, these z-values are constant (reflect light in only one direction) and therefore form a plane, such as the plane M (FIG. 3) in the image volume. Deviation of the extracted z-values from the constant M, i.e. the difference in reflection angles between part-surface in question and the ideal surface, is a measurement of the gloss quality in this type of gloss quality determining process. If the part-surface is approximated to be considered as consisting of one gloss facet, the aforesaid deviation will be a measurement of the slope of the facet in relation to the ideal flat surface; c.f. for instance the slope of the part-surface A3 at the angle V3 relative to the normal N of the "ideal surface" in FIG. 4.

Figure 7:
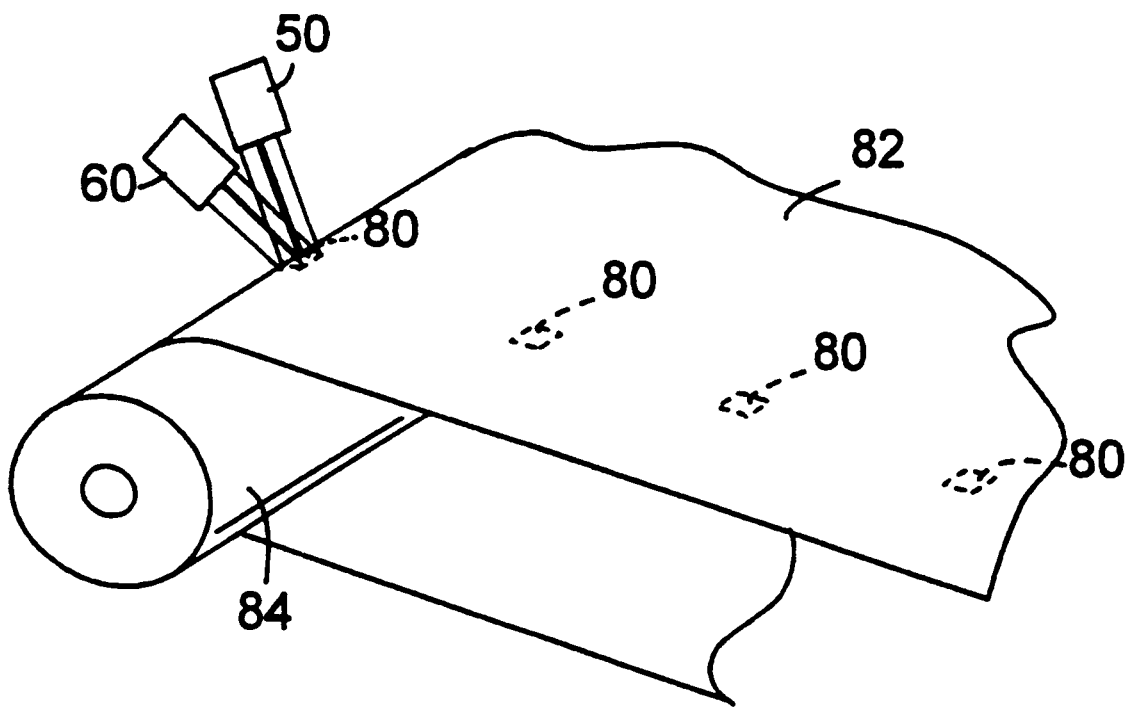
FIG. 7 illustrates schematically parts of an apparatus arranged for determining the gloss quality of a moving web, according to the invention.

FIG. 7 illustrated another type of gloss quality determination in accordance with the invention which can be carried out on a curved surface, e.g. in the region of a direction deflecting roll 84, of a sample in the form of a moving web 82 in a laboratory or during production, in the latter case as the basis on which the gloss quality of rapidly moving paper, e.g. on a fast printing machine, can be controlled. In this case, planes in the image volume can be used as a statistical basis for enabling the measuring results to be evaluated more quickly than if the whole image volume would be considered. More specifically, a full sample surface 80 (c.f. FIG. 6C) can be registered each time as indicated schematically in FIG. 7, and the sample surface replace by a fresh sample surface 80 of the sample 82 prior to each new registration, thereby obtaining the intensity values in a diagonal plane, such as an x+z constant, in the image volume on each occasion. In this regard, both undesired intensity distributions within separate sample surface 80 and undesired intensity distribution variations between sample surfaces 80 can be registered.

Another type of gloss quality determining process may concern the gloss intensity at viewing angles off the specular reflection. In this case, the z-interval (interval of viewing angles) around the z-value of Imax, where the intensity I exceeds a specific threshold value, may for each picture element be searched.

The threshold value can be chosen at the intensity where, e.g., an examiner finds it difficult to discern printed information on a paper surface.

Other methods of creating measurements of gloss quality from the image volume created through the invention may include different types of electronic or optical filtering processes based on known information relating to the mechanisms of human perception.

What is claimed is:

1. A method of obtaining a basis on which the gloss quality of a sample surface of a sample, such as a paper sheet, can be determined by illuminating the sample surface and registering the intensity of the light reflected thereby, which comprises exposing the sample surface in an image registering area by one of the steps of 1) controlled rotary movement of the sample surface through the image registering area, and 2) controlled rotary movement of the image registering area over and around the sample surface; and by registering the intensity of the light reflected by a plurality of spatially well defined part-surfaces of the sample surface a number of times during said rotary movement, while determining, at the same time, the positions of respective part-surfaces in the image registering area such as to compile an image volume that represents the registered light intensity as a function of the position of the part-surfaces within the sample surface and of the respective viewing angle.

2. A method according to claim 1, which includes the step of bringing the sample surface to a specific convex-curved shape prior to exposing the surface in the image registering area.

3. A method according to claim 1 wherein said sample surface is circular-cylindrical in shape and is exposed in the image registering area by rotational movement around the axial centre of the cylindrical surface.

4. A method according to claim 3 comprising effecting said rotary movement in steps and effecting said registration between said steps.

5. A method according to claim 1 including the step of storing the image volume in a data base for separate determination of the gloss quality according to defined criteria for such quality.

6. A method according to claim 1 which comprises registering the intensity of the light reflected during said rotary movement several times from each part-surface.

7. A method according to claim 1 which comprises registering the intensity of the reflected light during said rotary movement only once from each part-surface of a plurality of sample surfaces of the sample.

8. Apparatus for obtaining a basis on which the gloss quality of a sample surface of a sample, such as a paper sheet, can be determined by illuminating the sample surface and registering the intensity of the light reflected thereby, comprising means for exposing the sample surface in an image registration area by controlled rotary movement of the sample surface through the image registering area or by controlled rotary movement of the image registering area over and around the sample surface, and by means for registering the intensity of the light reflected from a number of spatially well defined part-surfaces of the sample surface during said rotary movement while, at the same time, determining the positions of respective part-surfaces in the image registering area, such as to compile an image volume that represents registered light intensity as a function of the position of the part-surfaces within the sample surface and of the respective viewing angle.

9. Apparatus according to claim 8, wherein said sample surface exposure means includes a stationary light source and a rotatably driven sample holder.

10. Apparatus according to claim 9, wherein said sample holder is constructed to expose a sample having a convex-curved sample surface in the image registering area.

11. Apparatus according to claim 10, wherein said sample surface is circular-cylindrical in shape; and in that its cylinder axis coincides with the rotational axis of the sample holder.

12. Apparatus according to claim 8, wherein said sample holder is driven by a stepping motor.

13. Apparatus according to claim 8, wherein said registering means includes a camera which is adapted to send the detected information to an image processing unit.

14. Apparatus according to claim 13, wherein said image processing unit is adapted to control said rotary movement.

15. Apparatus according to claim 8, wherein said sample is a paper web; and in that the sample holder includes a paper-web deflecting roll, allowing analysis of a continuous paper web.

* * * * *